United States Patent
Fink

(10) Patent No.: US 8,148,523 B2
(45) Date of Patent: Apr. 3, 2012

(54) INTERMEDIATES USEFUL IN PREPARING CERTAIN PYRROLOTRIAZINE COMPOUNDS AND A PROCESS FOR MAKING THE INTERMEDIATES

(75) Inventor: Brian E. Fink, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 385 days.

(21) Appl. No.: 12/522,315

(22) PCT Filed: Jan. 7, 2008

(86) PCT No.: PCT/US2008/050362
§ 371 (c)(1),
(2), (4) Date: Jul. 7, 2009

(87) PCT Pub. No.: WO2008/086264
PCT Pub. Date: Jul. 17, 2008

(65) Prior Publication Data
US 2010/0056781 A1    Mar. 4, 2010

Related U.S. Application Data

(60) Provisional application No. 60/883,850, filed on Jan. 8, 2007.

(51) Int. Cl.
*C07D 487/04* (2006.01)
*A61K 31/53* (2006.01)
(52) U.S. Cl. ........................................ 544/183; 514/243
(58) Field of Classification Search .................. 544/183; 514/243
See application file for complete search history.

(56) References Cited

U.S. PATENT DOCUMENTS

| 7,232,901 B2 * | 6/2007 | Mastalerz et al. ............ 544/183 |
| 7,619,083 B2 * | 11/2009 | Mastalerz et al. ............ 544/183 |
| 2006/0030708 A1 | 2/2006 | Lobben |
| 2006/0084650 A1 | 4/2006 | Dong et al. |
| 2007/0004734 A1 * | 1/2007 | Mastalerz et al. ............ 514/243 |

FOREIGN PATENT DOCUMENTS

| WO | WO 2005/037838 | 4/2005 |
| WO | WO 2007/005709 | 1/2007 |

* cited by examiner

*Primary Examiner* — Venkataraman Balasubramanian
(74) *Attorney, Agent, or Firm* — Elliott Korsen

(57) ABSTRACT

The invention relates to 4-chloro-2-iodopyrrolo[1,2-f][1,2,4]triazine, which is an intermediate useful in preparing 2,4-disubstituted pyrrolotriazine compounds, and a process for preparing said intermediate.

5 Claims, No Drawings

INTERMEDIATES USEFUL IN PREPARING CERTAIN PYRROLOTRIAZINE COMPOUNDS AND A PROCESS FOR MAKING THE INTERMEDIATES

FIELD OF THE INVENTION

The invention generally relates to 4-chloro-2-iodomopyrrolo[1,2-f][1,2,4]triazine, which is an intermediate useful in preparing 2,4-disubstituted pyrrolotriazine compounds, and a process for making said intermediate. The compound of the invention is an intermediate used in the preparation of compounds that may be useful for the treatment of cancer.

BACKGROUND OF THE INVENTION

Hyperproliferative diseases, such as, cancer are generally characterized by uncontrolled cellular proliferation and/or disruption in programmed cell death. Uncontrolled cellular proliferation is often caused by genetic damage to cellular pathways responsible for regulating cellular functions, such as, metabolism, cell cycle progression, cell adhesion, vascular function, apoptosis, and angiogenesis. As a result, one approach utilized in treating hyperproliferative diseases has involved targeting at least one protein involved in regulating cellular functions.

The protein kinase(s) (PK(s)) are a class of proteins that have been identified as playing an important role in regulating cellular functions. Indeed, many diseases are associated with abnormal cellular responses triggered by PK-mediated events. Such diseases include, but are not limited to, for example, autoimmune diseases, bone diseases, inflammatory diseases/disorders, metabolic diseases, neurological and neurodegenerative diseases, cancer, cardiovascular diseases, allergies and asthma, Alzheimer's disease, and hormone related diseases.

The PKs are a large and diverse group of enzymes that can be divided into groups based on the particular amino acids (serine/threonine, tyrosine, lysine, and histidine) targeted by each PK. For example, receptor and non-receptor tyrosine kinases target tyrosine, whereas cyclin dependent kinases (CDKs) and mitogen activated protein kinases (MAPKs) target both tyrosine and serine/threonine.

Exemplary PKs include, but are not limited to, receptor tyrosine kinases (RTKs); non-receptor tyrosine kinases or cellular tyrosine kinases (CTKs); serine/threonine kinases (STKs); cyclin dependent kinases (CDKs); and mitogen-activated protein kinases (MAPKs).

Exemplary RTKs include, but are not limited to, type III RTKs, such as, Flt3; "HER" RTKs, such as, epithelial growth factor receptor (EGFR), HER2, HER3, and HER4; C-MET; insulin receptor (IR); insulin-like growth factor 1 receptor (IGF-1R) and its ligands IGF-1 and IGF-2; insulin receptor related receptor (IRR); platelet derived growth factor receptors (PDGFRs), such as, PDGFRα, PDGFRβ, CSFIR, c-kit, and c-fms; fetus liver kinases (flks), such as, kinase insert domain-receptor fetal liver kinase-1 (KDR/FLK-1, VEGF-R2), flk-1R, flk-4, and fms-like tyrosine kinase 1 (flt-1); fibroblast growth factor (FGF) receptors, such as, FGFR1, FGFR2, FGFR3, and FGFR4 and FGF ligands, such as, FGF1, FGF2, FGF3, FGF4, FGF5, FGF6, and FGF7; vascular endothelial growth factor receptors (VEGFRs), such as, VEGFR1, VEGFR2, and VEGFR3; Tie receptors, such as from example, Tie2; and Trk receptors, such as, TrkA, TrkB, and TrkC. For a more detailed discussion of RTKs, see Plowman et al., *KN&P,* 7(6):334-339 (1994).

Exemplary CTKs include, but are not limited to, Src kinases, such as, Src, Yes, Fyn, Lyn, Lck, Blk, Hck, Fgr, and Yrk; Frk kinases; Btk kinases; Csk kinases; Abl kinases; ZAP70 kinases; Fes kinases; Fps kinases; Fak kinases; Jak kinases; Ack kinases; and Kak kinases. For a more detailed discussion of known CTKs, see Bolen, *Oncogene,* 8:2025-2031 (1993).

Exemplary STKs include, but are not limited to, p90 ribosomal S6 kinases (RSKs), such as, RSK1/p90Rsk, RSK2, RSK3, and RSK4; checkpoint protein kinases, such as, CHK1 and CHK2; Aurora kinases, such as, aurora-A, aurora-B, and aurora-C; and Glycogen synthase kinase 3 (GSK3).

Exemplary CDKs include, but are not limited to, CDK1; CDK2; CDK4; CDK5; CDK6 and CDK 7; and cell division control 2 proteins (CDC2);

Exemplary MAPKs include, but are not limited to, MAPK 1 (ERK); MAPK3; MAPK7; MAPK 8 (JNK1); MAPK 14 (p38α); MAPK 10; JNK 3 a protein kinase; stress-activated protein kinase JNK 2; and MAPK 14.

In view of the link between PK-related cellular activities and a wide variety of human disorders, including, cancer, and the discovery that certain pyrrolotriazine-containing compounds exhibit inhibitory activity of at least one PK, such pyrrolotriazine-containing compounds were found to be useful in treating conditions associated with abnormal PK activity.

2,4-Dichloropyrrolo[1,2-f][1,2,4]triazine, as an intermediate for the preparation of certain pyrrolotriazine compounds, is disclosed in U.S. Ser. No. 11/426,707, filed Jun. 27, 2006. 2,4-Disubstituted pyrrolotriazine compounds are disclosed in, for example, the following provisional patent applications, U.S. Ser. No. 11/773,466, U.S. Ser. No. 11/835,456, U.S. Ser. No. 11/835,469, and PCT/US2007/083436.

SUMMARY OF THE INVENTION

Described herein is the compound of formula I,

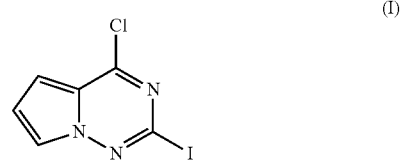

or a pharmaceutically acceptable salt thereof.

Further described herein is a process for preparing the compound of Formula I or a pharmaceutically acceptable salt thereof comprising reacting compound A of the formula,

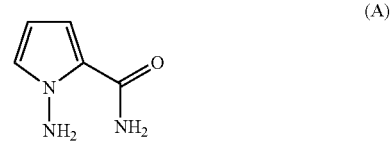

with benzoylisothiocyanate in a solvent to afford Compound B of the formula

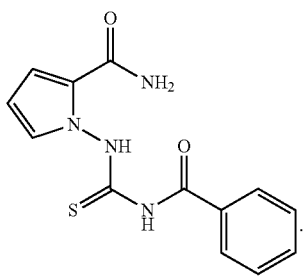

Compound B is hydrolyzed in aqueous media to afford Compound C of the formula

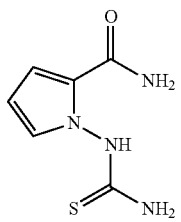

which is cyclized to afford Compound D of the formula

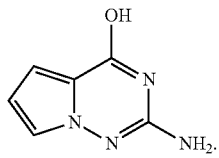

Compound D can be reacted with n-pentylnitrite, followed by a halide source, such as diiodomethane, to afford Compound E of the formula

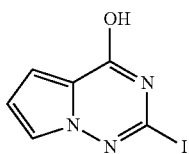

which can be treated with a chlorinating agent in the presence of a base to afford Compound I, or a pharmaceutically acceptable salt thereof.

DETAILED DESCRIPTION OF THE INVENTION

The features and advantages of the invention may be more readily understood by those of ordinary skill in the art upon reading the following detailed description.

The compound of Formula I can also form salt(s). Exemplary acidic salt(s) of Formula I can form with inorganic and/or organic acids include, but are not limited to, for example, acetates, such as are formed with acetic or trihaloacetic acid; adipates; alginates; ascorbates; aspartates; benzoates; benzenesulfonates; bisulfates; borates; butyrates; citrates; camphorates; camphorsulfonates; cyclopentanepropionates; digluconates; dodecylsulfates; ethanesulfonates; fumarates; glucoheptanoates; glycerophosphates; hemisulfates; heptanoates; hexanoates; hydrochlorides; hydrobromides; hydroiodides; hydroxyethanesulfonates, such as, for example, 2-hydroxyethanesulfonates; lactates; maleates; methanesulfonates; naphthalenesulfonates, such as, for example, 2-naphthalenesulfonates; nicotinates; nitrates; oxalates; pectinates; persulfates; phenylpropionates, such as, for example, 3-phenylpropionates; phosphates; picrates; pivalates; propionates; salicylates; succinates; sulfates, such as, for example, are formed with sulfuric acid; sulfonates; tartrates; thiocyanates; and toluenesulfonates, such as, for example, tosylates and undecanoates. Such salts can be formed in accordance with methods known to a person of ordinary skill in the art.

Exemplary basic salt(s) that compounds of Formula I can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, hydrabamines (such as, for example, N,N-bis(dehydroabietyl) ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), and aralkyl halides (e.g. benzyl and phenethyl bromides) to quaternize basic nitrogen-containing groups. Such salts can be formed in accordance with methods known to a person of ordinary skill in the art.

In general, the compound of formula I can be prepared in accordance with Scheme 1 and the general knowledge of one skilled in the art.

Scheme 1

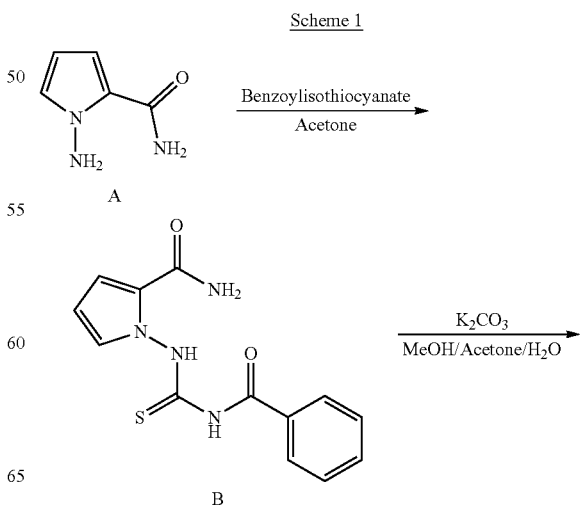

-continued

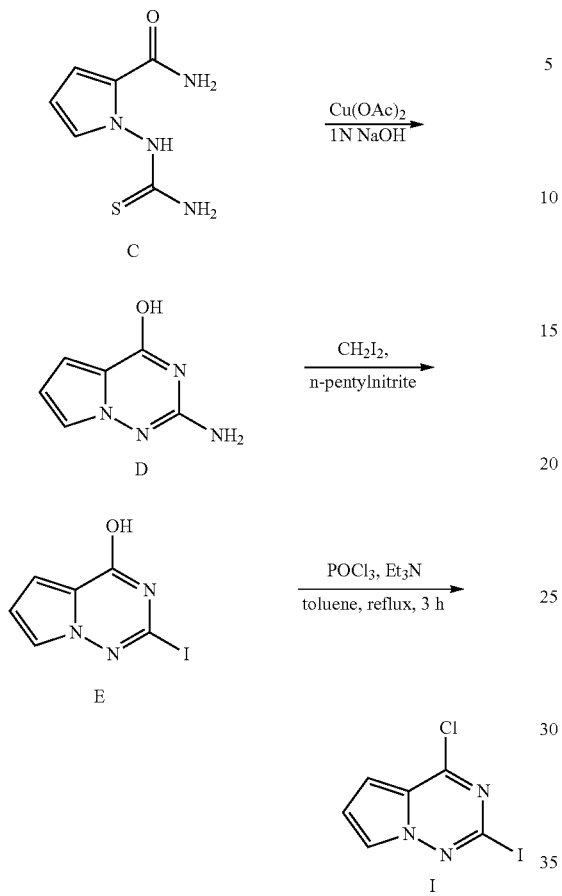

Step 1

Compound B can be prepared by reacting 1-aminopyrrole-2-carboxamide (*J. Heterocyclic Chemistry* 1994, 31, 781-6) with benzoylisothiocyanate in an appropriate solvent such as acetone. Hydrolysis of B in aqueous media affords compound C, which may be cyclized to afford compound D using Cu(OAc)$_2$ in aqueous sodium hydroxide solution. Compound D can be converted to compound E through diazotization of the C-2 amino group with n-pentylnitrite followed by displacement with an appropriate halide source such as diiodomethane. Treatment of compound E with POCl$_3$ in the presence of base can be used to produce compound I. The reactions in Scheme 1 can be carried out in accordance with methods readily known to a person of ordinary skill in the art.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather defined by the claims appended hereto.

All temperatures are in degrees Celsius (° C.) unless indicated otherwise herein.

Example 1

4-chloro-2-iodopyrrolo[1,2-f][1,2,4]triazine

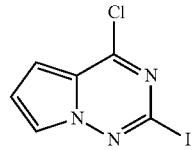

1A. Preparation of 1-(3-benzoylthioureido)-1H-pyrrole-2-carboxamide

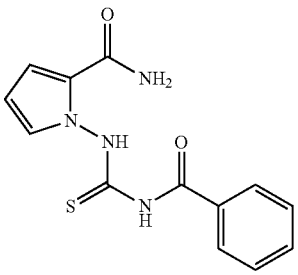

A solution of benzoylisothiocyanate (1.2 mL, 8.8 mmol) in acetone (10 mL) was treated with 1-aminopyrrole-2-carboxamide (1.0 g, 8.0 mmol) at ambient temperature. The resulting suspension was stirred for one hour and then cooled to 0° C. The solid material was collected by vacuum filtration and washed with diethyl ether before drying under high vacuum to afford 1A (2.2 g, 96%). HPLC tR=2.55 min (YMC S5 Combiscreen ODS 4.6×50 mm, 10-90% aqueous methanol containing 0.2% H$_3$PO$_4$, 4 min gradient, monitored at 254 nm). [M+H]$^+$=289.29. $^1$H NMR (400 MHz, DMSO-d$_6$) δ 12.9 (s, 1H), 11.9 (s, 1H), 8.0 (dd, 2H, J=1.2, 7.2 Hz), 7.68 (t, 1H, J=7.6 Hz), 7.55 (m, 3H), 7.03 (s, 1H), 6.92 (br s, 1H), 6.82 (dd, 1H, J=1.6, 4.0 Hz), 6.11 (dd, 1H, J=3.2, 4.0 Hz).

1B. Preparation of 1-thioureido-1H-pyrrole-2-carboxamide

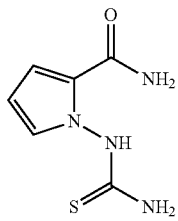

Compound 1A (2.2 g, 7.6 mmol) was treated with a solution of K$_2$CO$_3$ (2.0 g, 14.8 mmol) in water (9 mL) at ambient temperature. Methyl alcohol (70 mL) and acetone (70 mL) were added and the mixture was heated to reflux for 18 hours. The reaction was cooled to ambient temperature and treated with acetic acid (2.0 mL, 35 mmol), and then concentrated to approximately 30 mL. The resulting suspension was cooled to 0° C. and the product was recovered by vacuum filtration to afford 1B (1.1 g, 79%). HPLC tR=0.405 min (YMC S5 Combiscreen ODS 4.6×50 mm, 10-90% aqueous methanol containing 0.2% H$_3$PO$_4$, 4 min gradient, monitored at 254 nm). $^1$H NMR (400 MHz, DMSO-d$_6$) δ 10.4 (s, 1H), 8.13 (br s, 2H), 7.31 (br s, 1H), 7.10 (br s, 1H), 6.88 (t, 1H, J=2.0 Hz), 6.75 (dd, 1H, J=1.6, 4.0 Hz), 6.05 (t, 1H, J=3.6 Hz).

1C. Preparation of 2-aminopyrrolo[1,2-f][1,2,4]triazin-4-ol

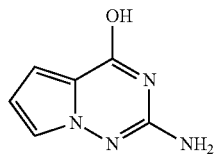

A solution of 1B (1.1 g, 6.0 mmol) in 1N NaOH (35.9 mL, 35.9 mmol) was treated with Cu(OAc)$_2$—H$_2$O (1.3 g, 6.8 mmol) and heated to 85° C. for 90 minutes. The resulting suspension was cooled to ambient temperature and filtered through a pad of celite. The celite pad was washed with 1N NaOH (10 mL) and the filtrate was collected. The clear filtrate was treated with glacial acetic acid until pH 6 was reached and the resulting suspension was cooled to 0° C. for one hour. The precipitated product was collected via vacuum filtration and dried under high vacuum to afford 1C (780 mg, 87%). HPLC tR=1.228 min (YMC S5 Combiscreen ODS 4.6×50 mm, 10-90% aqueous methanol containing 0.2% H$_3$PO$_4$, 4 min gradient, monitored at 254 nm). $^1$H NMR (400 MHz, DMSO-d$_6$) δ 10.6 (s, 1H), 7.22 (t, 1H, J=2.0 Hz), 6.69 (dd, 1H, J=1.2, 4.0 Hz), 6.30 (dd, 1H, J=2.4, 4.4 Hz), 5.82 (s, 2H).

1D. Preparation of 2-iodopyrrolo[1,2-f][1,2,4]triazin-4-ol

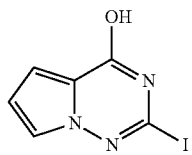

A solution of 1C (100 mg, 0.7 mmol) in CH$_2$I$_2$ (3 mL) was treated with n-pentylnitrite (0.6 mL) at 0° C. The reaction was warmed to 80° C. and stirred for one hour, and then cooled to ambient temperature. The solvents was removed under reduced pressure and the residue was taken up in CH$_2$Cl$_2$ and filtered to afford the desired 1D (58 mg, 33%). HPLC tR=2.213 min (YMC S5 Combiscreen ODS 4.6×50 mm, 10-90% aqueous methanol containing 0.2% H$_3$PO$_4$, 4 min gradient, monitored at 254 nm). [M+H]$^+$=262.23. $^1$H NMR (400 MHz, DMSO-d$_6$) δ 12.3 (s, 1H), 7.58 (s, 1H,), 6.87 (t, 1H, J=2.8 Hz), 6.46 (s, 1H).

1E. Preparation of 4-chloro-2-iodopyrrolo[1,2-f][1,2,4]triazine (Compound of Formula I)

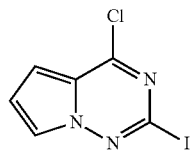

A solution of 1D (50 mg, 0.19 mmol) in toluene (2 mL) was treated with POCl$_3$ (0.02 mL, 0.23 mmol) and Et$_3$N (0.023 mL, 0.17 mmol). The reaction mixture was heated to reflux for three hours and additional POCl$_3$ (0.02 mL, 0.23 mmol) was added. After an additional three hours at reflux the reaction was cooled to ambient temperature and poured into ice cold saturated aqueous NaHCO$_3$. The mixture was extracted with EtOAc (3×15 mL) and the combined organic layers were dried (Na$_2$SO$_4$), filtered and then concentrated to dryness to afford 1E (43 mg, 81%). HPLC tR=3.205 min (YMC S5 Combiscreen ODS 4.6×50 mm, 10-90% aqueous methanol containing 0.2% H$_3$PO$_4$, 4 min gradient, monitored at 254 nm). [M+H]$^+$=280.16.

I claim:

1. A compound of the formula

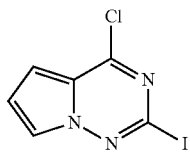

or a pharmaceutically acceptable salt thereof.

2. A process for preparing a compound I of the formula,

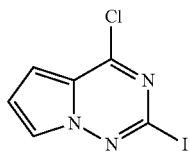

or a pharmaceutically acceptable salt thereof, comprising reacting Compound A of the formula

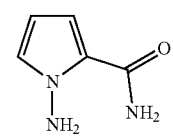

with benzoylisothiocyanate in a solvent to afford Compound B of the formula

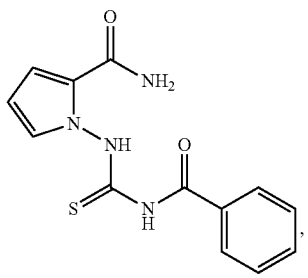

hydrolyzing Compound B in aqueous media, to afford Compound C of the formula

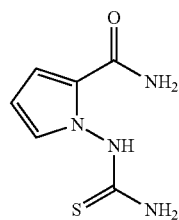

cyclizing Compound C to afford Compound D of the formula

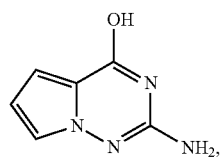

reacting Compound D with n-pentylnitrite, followed by a halide source to afford Compound E of the formula

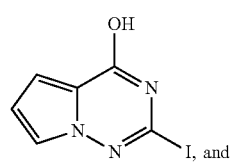

treating Compound E with a chlorinating agent in the presence of a base to afford Compound I.

3. The process according to claim 2, wherein the halide source is diiodomethane.

4. The process according to claim 2, wherein the chlorinating agent is phosphorous oxychloride.

5. A process for preparing a compound I of the formula,

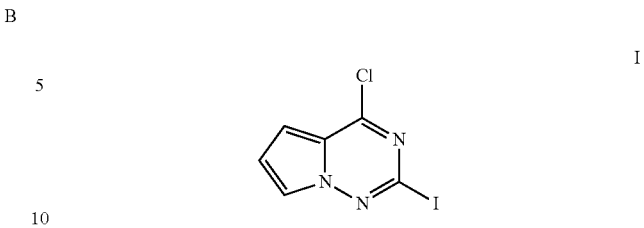

or a pharmaceutically acceptable salt thereof, comprising reacting Compound A of the formula

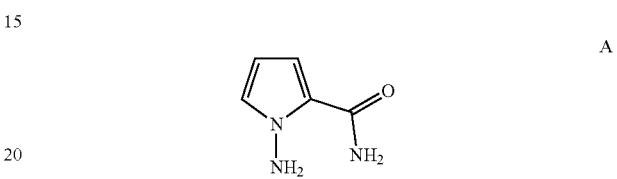

with benzoylisothiocyanate in a solvent to afford Compound B of the formula

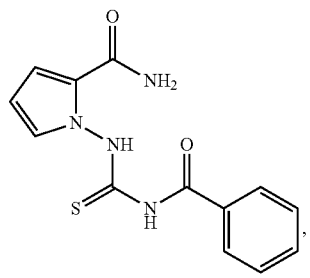

hydrolyzing Compound B in aqueous media, to afford Compound C of the formula

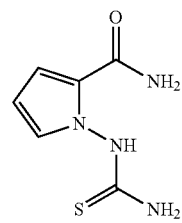

cyclizing Compound C to afford Compound D of the formula

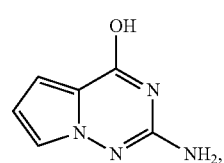

reacting Compound D with n-pentylnitrite, followed by a halide source, which is diiodomethane, to afford Compound E of the formula

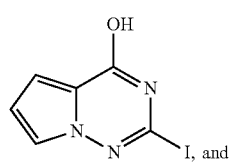 I, and
treating Compound E with a chlorinating agent, which is phosphorous oxychloride, in the presence of a base to afford Compound I.
* * * * *